United States Patent [19]

Zhou et al.

[11] Patent Number: 6,060,313
[45] Date of Patent: May 9, 2000

[54] METHODS FOR CLONE-MULTIPLICATION OF PAPHIOPEDILUMS

[75] Inventors: Tian Su Zhou, Nitta-machi; Michio Tanaka, Kagawa-ken, both of Japan

[73] Assignee: Sapporo Breweries Limited, Tokyo, Japan

[21] Appl. No.: 08/849,221

[22] PCT Filed: Oct. 16, 1996

[86] PCT No.: PCT/JP96/02998

§ 371 Date: Jun. 10, 1997

§ 102(e) Date: Jun. 10, 1997

[87] PCT Pub. No.: WO97/14295

PCT Pub. Date: Apr. 24, 1997

[30] Foreign Application Priority Data

Oct. 17, 1995 [JP] Japan ................................ 7-293329

[51] Int. Cl.[7] .................................................. C12N 5/00
[52] U.S. Cl. .......................................... 435/420; 47/58.1
[58] Field of Search .............................. 435/420; 47/58.1

[56] References Cited

FOREIGN PATENT DOCUMENTS 1095758  12/1964  United Kingdom .

OTHER PUBLICATIONS

K. Kawase, "Multiplication of Paphiopedilums by Tissue Cultures", J. J. Soc. Hort. Sci, 63(Suppl. 1), 1988 with Abridged Translation.

Li–Chun Huang, "A Procedure for Asexual Multiplication of Paphiopedilums in Vitro", American Orchid Society Bulletin, vol. 57, pp. 274–278, 1988.

Prakash Lakshmanan et al., "An In Vitro Method for Rapid Regeneration of a Monopodial Orchid Hybrid Aranda Deborah Using Thin Section Culture", Plant Cell Reports, vol. 14, pp. 510–514, (1995).

Database WPI, Section Ch, Week 8939, Derwent Publications Ltd., London, GB, AN 89–282442, XP002084843 & JP 01 206991 A, Aug. 21, 1989.

Shoji Kazuhiko, "Tissue Culture of Plant of Family Orchidaceae", Patent Abstracts of Japan, vol. 095, No. 001, Feb. 28, 1995.

K. Zimmer "Phalaenopsis—Zur Vegetativen Vermehrung", vol. 79, No. 11, pp. 258–260, 1979. (English Abstract Provided).

*Primary Examiner*—Leon B. Lankford, Jr.
*Attorney, Agent, or Firm*—Oblon, Spivak, McClelland, Maier & Neustadt, P.C.

[57] ABSTRACT

The present invention provides a method for clone-multiplication of a Paphiopedilum wherein a scape terminal bud or an axillary shoot, whose surface has been sterilized, or an aseptic shoot obtained by an aseptic cultivation, of a Paphiopedilum stock, are cut into cross-sectional pieces which are then cultivated in a medium containing a plant hormone. By cutting an aseptic shoot containing a number of axillary buds into cross-sectional pieces and cultivating, a multishoot formation is feasible. Also by employing a liquid medium containing a solid support such as a rockwool or a paper filter in the culture, the plant death due to browning of tissues can effectively be prevented. In addition, by optimizing the method for sterilizing the buds before blooming, the medium composition and the culture condition, a large scale production of Paphiopedilums by means of a clone multiplication technology becomes feasible.

5 Claims, 1 Drawing Sheet

FIGURE
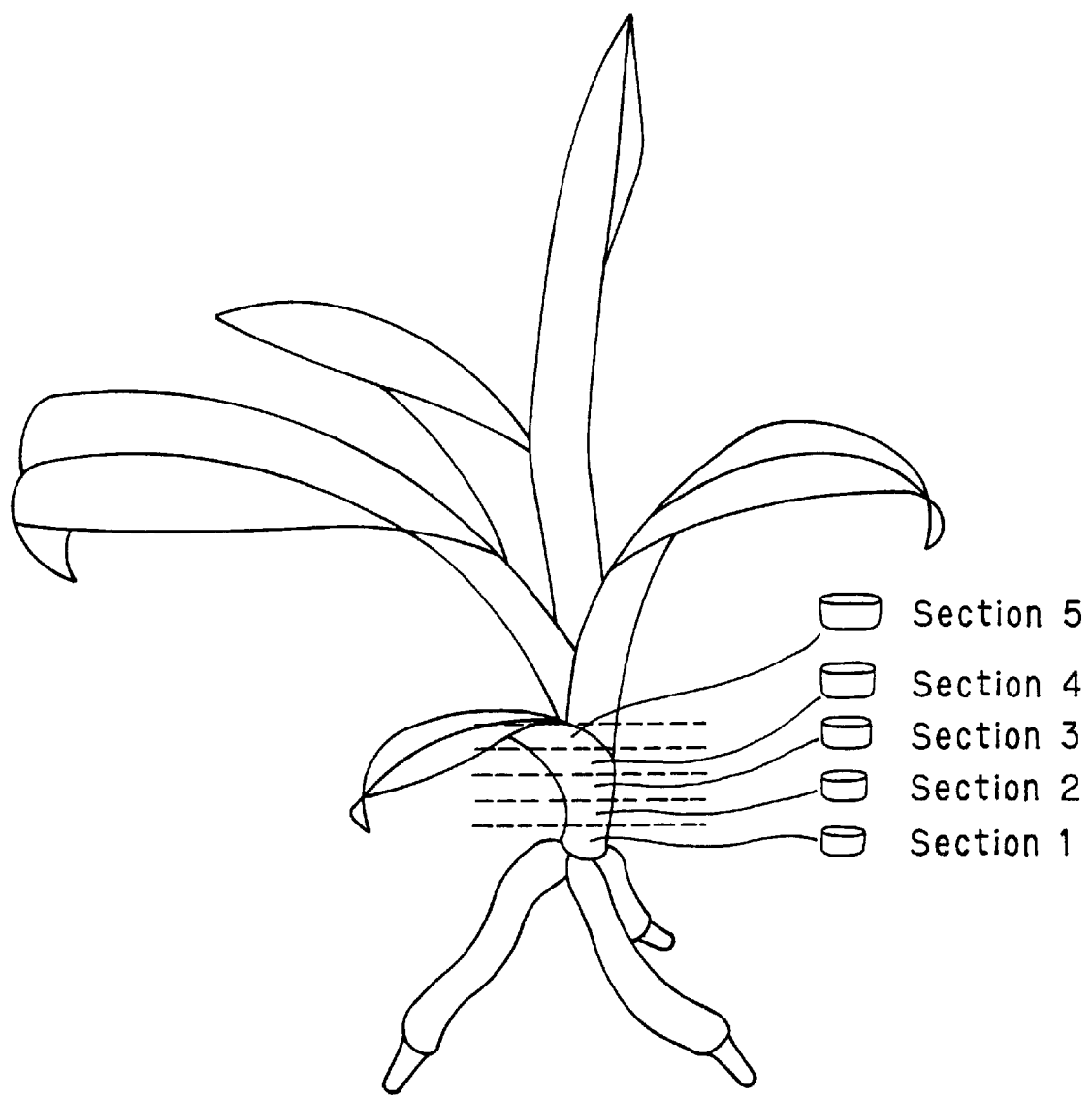

METHODS FOR CLONE-MULTIPLICATION OF PAPHIOPEDILUMS

FIELD OF TECHNOLOGY

The present invention relates to a method for producing the clone plants of Paphiopedilums in a large scale.

BACKGROUND TECHNOLOGY

Paphiopedilum is one of the most attractive garden plant in orchids. Studies in the prior art for establishing a clone multiplication technology of Paphiopedilums include a scape terminal bud culture method (K. Kawase, Multiplication of Paphiopedilums by tissue cultures, J. J. Soc. Hort. Sci. 63(Suppl.1), 1988), an axillary shoot culture method (L. C. Huang, A procedure for asexual for multiplication of Paphiopedilums in vitro, American Orchid Society Bulletin, 57: 274–278, 1988), a protocorm culture method (B. F. Mark, Tissue culture method for the genus Paphiopedilum. Australian Orchid Review, Feb. 4–10, 1991) and a shoot apex culture method (S. Yasuki et al., Meri-clone seedling formation of Paphiopedilums by a shoot apex culture method, Engeigakkaishi, 64 Extra number 1: 516–517, 1995).

However, if the multiplication of Paphiopedilum clone is carried out by such methods, there may be provided with low multiplication rate or no multiplication. Accordingly, such methods have suffered from difficulty in being employed as a practical technology for clone multiplication of Paphiopedilum.

The difficulty may be attributable to the plant death due to browning of tissues during culture as well as the missing of the combination of culture materials and culture conditions suitable for clone multiplication.

DISCLOSURE OF THE INVENTION

An objective of the present invention is to provide a method for producing a clone plants of a Paphiopedilum on a practical basis.

The first aspect of the present invention is a method for clone-multiplication of a Paphiopedilum wherein a scape terminal bud or an axillary shoot, whose surface has been sterilized, or an aseptic shoot obtained by an aseptic cultivation, are cut into cross-sectional pieces which are then cultivated in a medium containing a plant hormone.

The second aspect of the present invention is a method for clone-multiplication of a Paphiopedilum according to claim 1 wherein said medium in which said cross-sectional pieces are cultivated is a liquid medium containing a solid support capable of dispersing or adsorbing polymeric growth inhibiting substances, such as polyphenols, produced in said culture.

BRIEF DESCRIPTION OF DRAWINGS

FIG. 1 shows the preparation of the cross sectional pieces from a viable plant being cultured.

PREFERABLE EMBODIMENTS OF THE INVENTION

In a method according to the present invention, a starting material is a scape terminal bud derived from a blooming stock or a bud before blooming or a young axillary shoot. Cultivation of the scape terminal bud of a Paphiopedilum stock may be conducted, according to an ordinal condition, at an atmospheric temperature (usually 23 to 27° C., preferably at about 25° C.) under a continuous lighting or a 16-hour photoperiod. Such scape terminal bud cultivation is conducted preferably by an aseptic method. A scape terminal bud or an axillary bud obtained by a non-aseptic method should be employed after sterilizing its surface.

A scape terminal bud enclosed in a floral bud before blooming is preferably selected as a starting material, since it exhibits a higher survival rate after sterilization of the surface. In such case, a floral bud is taken from a Paphiopedilum and washed several times with an aqueous ethanol, preferably 70% ethanol in water, and then immersed 5 to 10 minutes, preferably for about 10 minutes, in an aqueous ethanol, preferably 70% ethanol in water, and subsequently shaken for about 10 minutes in a chlorinated sterilizing agent such as Wilson solution containing a surfactant such as Tween 20 at about 0.1%, whereby accomplishing sterilization of the surface, and then further washed several times with a sterilized water, resulting in a minimum contamination with environmental bacteria.

A scape terminal bud or an axillary shoot obtained by a non-aseptic method as mentioned above is employed as a starting material after sterilizing the surface, while an aseptic shoot obtained by an aseptic cultivation is employed as it is. The starting material is embedded in a culture medium and cultivated. When a scape terminal bud taken from a sterilized floral bud is employed, it is effective, for the purpose of prevention from the plant death due to browning, to reserve the scape at 0.5 to 1.0 cm from its base.

In the cultivation of a scape terminal bud or an axillary shoot employed in the present invention, a material capable of dispersing or adsorbing polymeric growth inhibiting substances, such as polyphenols, produced in the culture is employed as a solid support. Examples of the solid support employed preferably are rockwools and paper filters (Paperwick). In addition, a gellant such as Gellan gum is employed usually as a support, and, if necessary, an adsorbent such as polyvinylpyrrolidone (PVP), which has an inhibitory effect on browning, may also be added to the medium.

The medium may be a basal medium for plant tissue culture such as MS medium or ½ MS medium which is supplemented with a plant hormone. Examples of the plant hormone employed preferably are auxins such as naphthaleneacetic acid, which are employed usually in combination with cytokinins such as kinetin and benzyladenine.

Typically, the plant hormone-supplemented medium is prepared by adding 0.1 to 1.0 mg/L, preferably 0.5 mg/L of an auxin such as naphthaleneacetic acid (NAA), 0.3 to 10 mg/L, preferably 3 mg/L of a cytokinin such as benzyladenine (BA) and 20 g/L of sucrose, optionally together with about 10.0 mg/L of adenine, 10 to 15% of coconut water and 600 to 1,000 ppm, preferably about 800 ppm of PVP.

Addition of NAA and BA to the medium provides earlier growth of a shoot, while addition of PVP prevents plant death due to browning during the cultivation.

In a method according to the present invention, cross-sectional pieces can be prepared from an aseptic shoot obtained from the scape terminal bud or axillary shoot cultivation as described above. For example, an aseptic shoot having 3 to 5 developed leaves obtained by cultivating in the medium mentioned above for 3 to 5 months at 23 to 27° C., preferably at 25° C., under a light of 1000 to 4000 lux, preferably under 1700 lux with a photoperiod of 12 to 24 hours a day, preferably 16 hours, is preferably employed.

After removing the root of the aseptic shoot thus obtained, 4 to 6 pieces each having a thickness of about 2 mm are obtained by cutting the shoot into round slices from its base, and then embedded as the cross-sectional pieces in a medium for section cultivation.

In a method according to the present invention, as a support in a medium for section cultivation, a gellant such as Gellan gum is usually employed. In addition, a material capable of dispersing or adsorbing a polymeric growth inhibiting substance, such as polyphenols, produced in the culture is employed as a solid support. Examples of the solid support are rockwools and paper filters (Paperwick), and if necessary the medium is supplemented with PVP as an adsorbent for the purpose of inhibition of browning. An appropriate amount of Gellan gum to be added is 0.2 to 0.4%, and a rockwool, when employed, should be prepared so that its top becomes higher by about 1 cm than the surface of the liquid medium.

The medium employed in the section cultivation may be a basal medium for plant tissue culture such as MS medium or ½ MS medium, which is supplemented with 0.1 to 3.0 mg/L of an auxin such as naphthaleneacetic acid (NAA), 1 to 10 mg/L of a cytokinin such as kinetin and 15 g/L of sucrose, optionally together with about 10.0 mg/L of adenine, 10 to 15% of coconut water and 600 to 1,000 ppm, preferably about 800 ppm of PVP.

If the concentration of a plant hormone in the medium is low, no sufficient effect can be obtained, while a higher concentration causes adverse effect.

The cross-sectional pieces are embedded in the medium described above, and cultivated at 23 to 27° C., preferably at 25° C., under a light of 1000 to 4000 lux, preferably under 1700 lux with a lighting for a period of 12 to 24 hours a day, preferably 16 hours.

By cultivating for about 3 months under the condition detailed above, a multishoot can be formed from each section.

The multishoot thus formed is allowed to grow to 3 to 5 developed leaves, and then subjected to the preparation of the cross-sectional pieces, whereby repeating the cultivation of the cross-sectional pieces. In such a manner, a large scale multiplication of the clone plant of a Paphiopedilum can be achieved.

EXAMPLES

The present invention is further described in detail in the following examples.

Example 1

A scape terminal bud of a blooming stock of Paphiopedilums Sharmain and a bud of a stock before blooming were taken and washed their surfaces 3 times with 70% ethanol in water, and then immersed for 10 minutes in 70% ethanol in water. Subsequently, they were shaken for about 10 minutes in Wilson solution containing 0.1% Tween 20 to sterilize the surface, and then further washed 3 times with a sterilized water.

The sterilized scape terminal bud of the blooming stock and the scape terminal bud isolated from the sterilized floral bud of the stock before blooming thus obtained were processed while reserving the scales at 0.5 cm from the base of the scape terminal bud.

Then, 8 ml of the liquid medium consisting of ½ MS medium containing 0.2% Gellan gum and a rockwool (2.0 cm in diameter×3 cm in length) as the supports and 0.5 mg/L of NAA, 3 mg/L of BA and 20 g/L of sucrose together with about 10.0 mg/L of adenine, 15% of coconut water and about 800 ppm of PVP was placed in a culture tube of 2.5 cm in diameter×15 cm in depth, in which then the scape terminal bud of the blooming stock and that derived from the floral bud of the stock before blooming were embedded.

Subsequently, cultivation was conducted at 25° C. under 1700 lux of lighting for 16 hours a day. The results of the observation for shoot formation after 3 months are shown in Table 1.

TABLE 1

| Stage | Support | No. of samples | No. of shoots | No. of death by browing | No. of contamination |
|---|---|---|---|---|---|
| Blooming | Gellan gum | 22 | 3 | 16 | 3 |
|  | Rockwool | 22 | 14 | 4 | 3 |
| Before blooming | Gellan gum | 19 | 11 | 8 | 0 |
|  | Rockwool | 19 | 12 | 6 | 1 |

As evident from the table, the number of the shoot formed from the scape terminal bud derived from the stock before blooming was similar between the two supports, namely, Gellan gum and the rockwool, while the scape terminal bud derived from the blooming stock exhibited less browning and a larger number of the shoots when cultivated with the rockwool support.

Example 2

In the cultivation of the cross-sectional pieces from an aseptic shoot, a viable plant of a hybrid (Paphiopedilum Nettie×Paphiopedilum Maudiae) which had been grown by an aseptic cultivation to the stage of 3 to 5 developed leaves (equivalent to an aseptic shoot) was employed as a material, which was processed, after removal of the root, into 5 sections per seedlings, each having a thickness of about 2 mm, by cutting the shoot into round slices from its base (See FIG. 1).

Then, the cross-sectional pieces thus obtained were embedded on a medium consisting of 0.6% of agar, 0.2% of Gellan gum, a filter paper or a liquid medium as a support, combined with ½ MS medium supplemented with 1.0 mg/L of NAA, 3 mg/L of kinetin, 15 g/L of sucrose together with 10.0 mg/L of adenine, 15% of coconut water and about 800 ppm of PVP.

Subsequently, the cultivation was conducted at 25° C. under 1700 lux with the photoperiod of 16 hours a day. After 3 months, the pieces were examined for the shoot formation, and the results are shown in Table 2. In the table, the number of shoot-forming pieces represents the number of the pieces, out of the number of the pieces cultivated, which formed the shoots, while the total number of formed shoots represent the number of the shoots formed from the pieces cultivated.

When using a filter paper, Paperwick method was employed, wherein to a cultivation tube of 2.5 cm in diameter×15 cm in depth a cylindrical Paperwick of 2.0 cm in diameter×3 cm in length made from Whatman #2 filter paper and 8 ml of the liquid medium were placed. When using the liquid medium, the cultivation was conducted while rotating at 2 rpm.

TABLE 2

| Support | Total No. of sections | No. of shoot-forming sections | Total No. of shoot formed | No. of shoot/plant |
| --- | --- | --- | --- | --- |
| Agar | 50 | 4 | 4 | 0.4 |
| Gellan gum | 50 | 3 | 5 | 0.5 |
| Filter paper | 50 | 26 | 28 | 2.8 |
| Liquid medium | 50 | 1 | 1 | 0.1 |

Possibility of Industrial Utilization

According to the present invention, by cutting an aseptic shoot containing a number of axillary buds into cross-sectional pieces and cultivating, a multishoot formation is feasible.

Also by employing a rockwool or a paper filter as a support combined with a liquid medium containing a plant hormone in a scape terminal bud cultivation and a shoot cross section cultivation, the plant death due to browning of tissues can effectively be prevented.

In addition, by optimizing the method for sterilizing the buds before blooming, the medium composition and the culture condition, a large scale production of Paphiopedilums by means of a clone multiplication technology becomes feasible.

We claim:

1. A method for clone-multiplication of a Paphiopedilum wherein a scape terminal bud or an axillary shoot, whose surface has been sterilized, or an aseptic shoot obtained by an aseptic cultivation, or a Paphiopedilum stock, are cut into cross-sectional pieces which are then cultivated in a medium containing a plant hormone, wherein said medium in which said cross-sectional pieces are cultivated is a liquid medium containing a solid support capable of dispersing or adsorbing polymeric growth inhibiting substances, such as polyphenols, produced in said culture.

2. A method according to claim 1 wherein said scape terminal bud is derived from a floral bud before and/or after blooming.

3. A method according to claim 1 wherein said aseptic shoot is a plant having 3 to 5 developed leaves.

4. A method according to claim 1 wherein said medium contains naphthaleneacetic acid and kinetin or benzyladenine as plant hormones.

5. A method according to claim 1 wherein said medium contains polyvinylpyrrolidone together with said plant hormones.

* * * * *